United States Patent [19]
Ryan et al.

[11] Patent Number: 5,934,103
[45] Date of Patent: Aug. 10, 1999

[54] METHOD AND APPARATUS FOR PRODUCTION OF SPIN-POLARIZED MEDICAL-GRADE XENON [129] GAS BY LASER OPTICAL PUMPING

[75] Inventors: Robert E. Ryan, Levittown; John D. Hulsmann, Miller Place; Ron G. Pirich, Islip; Eric H. Schnittger, Smithtown; Theodore W. Hilgeman, Centerport, all of N.Y.

[73] Assignee: Northrop Grumman Corporation, Los Angeles, Calif.

[21] Appl. No.: 08/841,437

[22] Filed: Apr. 22, 1997

[51] Int. Cl.[6] .................................................. F25J 1/00
[52] U.S. Cl. ........................ 62/637; 62/55.5; 62/919; 62/925; 128/653.4; 204/157.22
[58] Field of Search ..................... 62/51.1, 55.5, 62/637, 919, 925; 128/653.4; 204/157.22

[56] References Cited

U.S. PATENT DOCUMENTS

| | | | |
|---|---|---|---|
| 3,569,705 | 3/1971 | Kaminsky | 250/84 |
| 3,700,899 | 10/1972 | Kaminsky | 250/84 |
| 4,617,462 | 10/1986 | Holt | 250/251 |
| 4,724,117 | 2/1988 | Stearns et al. | 376/129 |
| 5,617,860 | 4/1997 | Chupp et al. | 128/653.4 |
| 5,642,625 | 7/1997 | Cates, jr. et al. | 62/55.5 |

*Primary Examiner*—Ronald Capossela
*Attorney, Agent, or Firm*—Terry J. Anderson; Karl J. Hoch, Jr.

[57] ABSTRACT

Spin-polarized xenon gas is provided in medical-grade purity for use as a contrast medium in MRI studies by use of collision-induced transfer of spin energy to the xenon gas from laser-pumped spin-polarized Rb gas. The Rb gas is provided by thermally vaporizing solid Rb at low pressure in a container having an inside surface coated with a siliconizing agent and exposed to the Rb gas. The combined xenon and Rb gases are separated after transfer of the spin energy in order to provide a sufficient purity of the xenon gas by use of a cryogenic separation process. The Rb gas is removed from the xenon gas and is returned cryogenically to a solid stated to an acceptable level of purity for the xenon gas. The gas may be analyzed optically to measure the remaining Rb concentration.

20 Claims, 3 Drawing Sheets

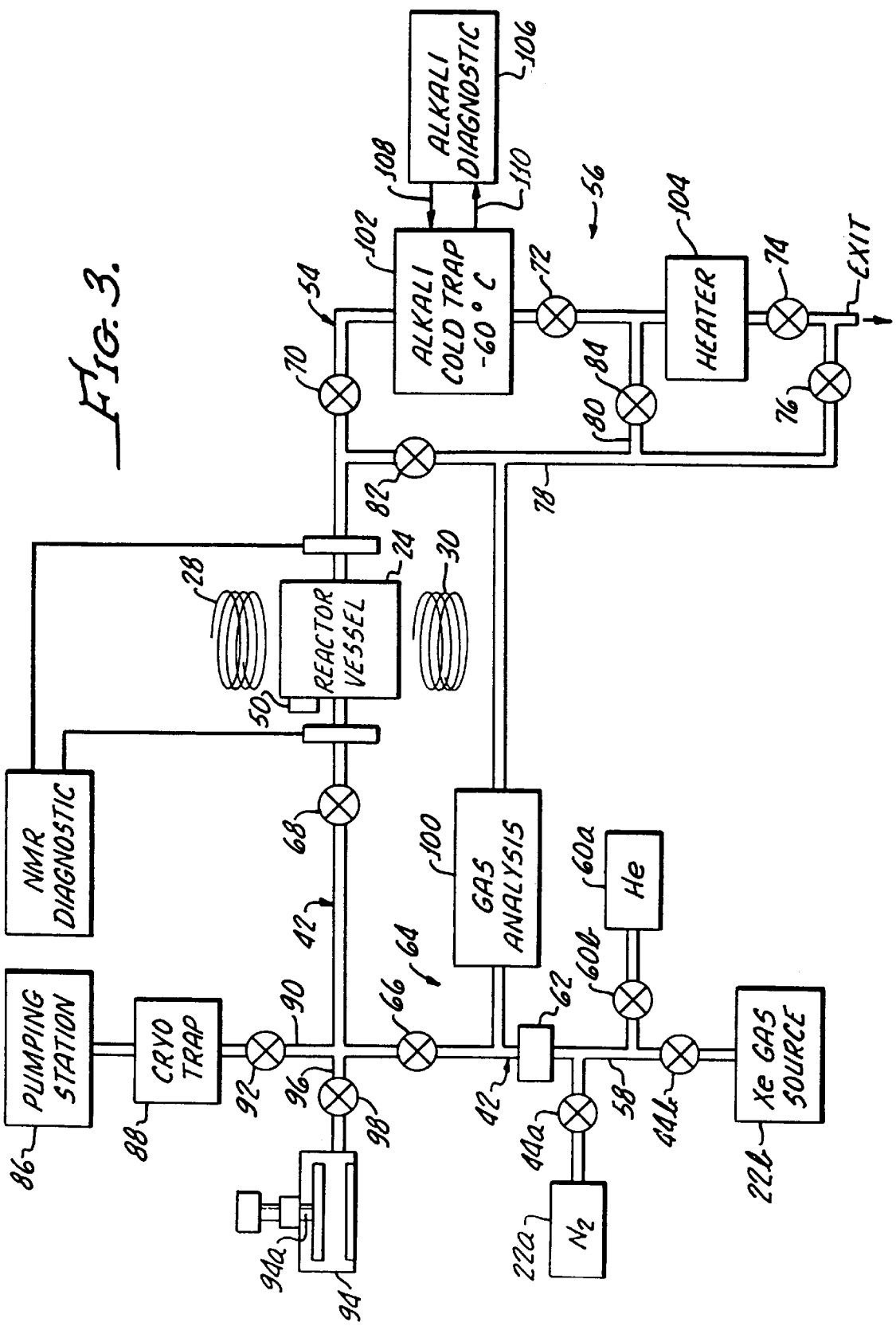

METHOD AND APPARATUS FOR PRODUCTION OF SPIN-POLARIZED MEDICAL-GRADE XENON $^{129}$ GAS BY LASER OPTICAL PUMPING

BACKGROUND OF THE INVENTION

1. Field of the Invention

The present invention relates to method and apparatus for providing spin-polarized medical-grade xenon$^{129}$ gas. That is, the spin-polarized xenon$^{129}$ gas provided by the present invention is of sufficient purity for use as a medical-grade contrast media in carrying out magnetic resonance imaging (MRI) procedures of lung and bronchial structures within a living human during which the living human inhales the xenon gas. The living human inhales a gas mixture including spin-polarized xenon$^{129}$ gas during a MRI procedure to improve the contrast of the MRI images. Thus, this invention also relates to medical procedures in which spin-polarized xenon$^{129}$ gas produced according to the teachings of the invention is utilized.

2. Related Technology

It is recognized that hyperpolarized (i.e., spin-polarized) xenon$^{129}$ gas is a significant contrast enhancement agent for use in magnetic resonance imaging (MRI) of human lung and bronchial structures in living humans. Potentially, there is a need for about 10 million such MRI procedures in the United States each year. These procedures could benefit from the improved contrast which would be provided were a medical grade of polarized xenon$^{129}$ gas to be readily available. Consumption of polarized xenon$^{129}$ gas would be in the range of from one to five grams of the gas for each such MRI procedure. Accordingly, for each facility performing such procedures, a few tens of grams of polarized xenon$^{129}$ gas would be required each day.

It has been thought that a potential way to provide spin-polarized xenon$^{129}$ gas is to first induce spin-polarization of rubidium (Rb) gas by use of laser pumping, and to exchange spin energy from the Rb gas to xenon gas to provide collision-induced polarization of the xenon gas. After the xenon gas is polarized, the two gases must be separated, and the spin-polarized xenon is then available for use as a contrast medium. However, prior to this invention a number of insurmountable problems have existed with this potential approach. First, because of the residue of Rb gas present in the xenon gas after the two gases are "separated", and which residue of Rb is toxic to human tissues, the spin-polarized xenon gas was not of medical-grade quality and was not usable in human treatment. Secondly, the efficiency with which laser optical pumping of the Rb gas could be effected was so low and the resulting power requirements for the laser equipment was so high (and therefore, costly) that the process could not be economically justified.

SUMMARY OF THE INVENTION

In view of the above, a primary object for this invention is to avoid one or more of the shortcomings of the conventional technology.

Another object for this invention is to provide a system for providing medical-grade spin-polarized xenon gas which is acceptable for use as a medical contrast medium because any existing residue of Rb gas has been reduced to acceptable levels.

A further object for this invention is to provide a system for spin-polarizing xenon$^{129}$ gas by collision-induced spin energy transfer from laser optical pumped Rb gas, and in which the laser power requirements are managed in such a way as to make possible the use of diode laser bars of acceptably low economic cost.

An advantage of the present invention resides in its use in one embodiment of diode laser bars. These diode laser bars consist of arrays of diode laser arrays. That is, the laser diodes of such a diode laser bar are arrayed in "fields" of such devices. While the energy conversion efficiency of such diode laser bars may not be as great as can be obtained with other forms of lasers, their mass production will make them extremely inexpensive, and thus will make the advantages of the present invention more widely available because of a more easily attainable price.

A better understanding of the present invention will be obtained from reading the following description of a single preferred exemplary embodiment of the present invention when taken in conjunction with the appended drawing Figures, in which the same features (or features analogous in structure or function) are indicated with the same reference numeral throughout the several views. It will be understood that the appended drawing Figures and description here following relate only to a single exemplary preferred embodiment of the invention, and as such, are not to be taken as implying a limitation on the invention. No such limitation on the invention is implied, and none is to be inferred.

BRIEF DESCRIPTION OF THE DRAWING FIGURES

FIG. 1 provides a somewhat schematic perspective view of a human patient undergoing magnetic resonance imaging of lung or bronchial tissues of the patient's body by use of spin-polarized xenon gas provided in accord with the teachings of the present invention;

FIG. 2 is a schematic representation of a system for providing spin-polarized xenon gas according to the teaching of the present invention;

FIG. 2a provides a fragmentary view like a portion of FIG. 2 but depicting an alternative embodiment of the invention;

FIG. 3 provides a more particularized and still somewhat schematic representation of apparatus for providing spin-polarized xenon gas according to the invention; and FIG. 4 provides a graphical representation of the result of a cryogenic method of separating Rb molecules from the mixed Rb and xenon gas flow.

DETAILED DESCRIPTION OF AN EXEMPLARY PREFERRED EMBODIMENT OF THE INVENTION

Figure 1:
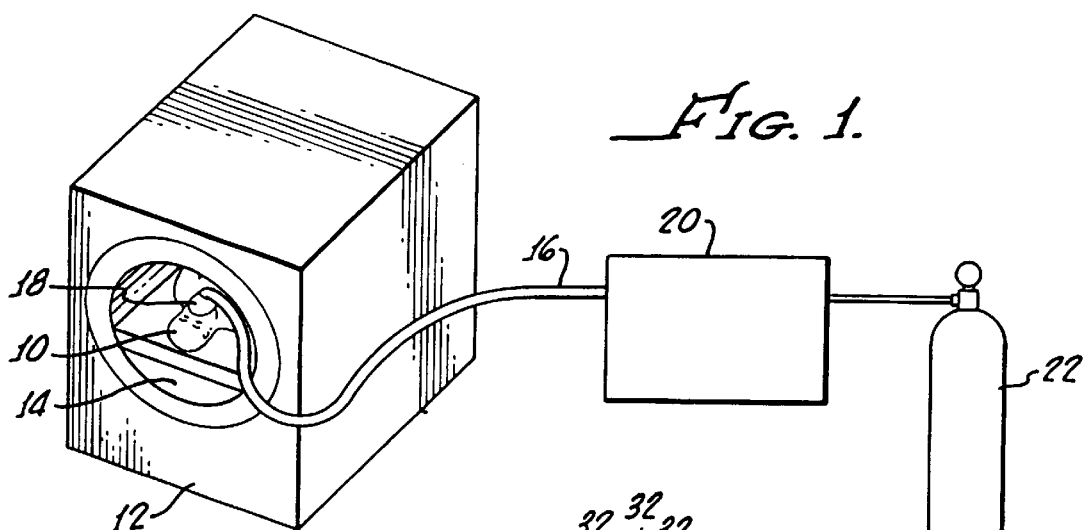

Viewing FIG. 1, a patient 10 is seen undergoing magnetic resonance imaging (MRI) of internal tissue structures of the patient. In order to accomplish this MRI imaging a tunnel type of MRI device 12 is being used, although the invention is not limited to this or any other particular type of MRI device. The particular MRI device 12 includes a tunnel 14 in which at least a part of the patient 10 is received. In this case, the upper torso portion of the patient's body is received into the tunnel 14 so that the MRI process may image the lung and bronchial tissue structures of the patient 10.

As explained, in this case the MRI process is to provide an image of the patient's lung or bronchial tissues. As is readily understood, these lung and bronchial tissues consist of many air passages and branchiae, in which the tissues receive and interface with air inhaled by the patient. Moreover, examination and diagnosis of such tissue structures inherently involves a consideration of the tissue-to-air interface of the tissues. With conventional MRI devices, this tissue-to-air interface is particularly difficult to image with desirable contrast.

In order to improve the contrast of the MRI images of the patients lungs and bronchial tissues in this case and according to the present invention, the patient 10 is provided via a tube 16 and mask 18 with a mixture of gases (i.e., a mixture of nitrogen, oxygen, water vapor, and other gases as will be explained below) which is inhaled by the patient 10 during the MRI procedure. One of the gases included in this mixture of gases received by the patient 10 during the MRI procedure is spin-polarized xenon$^{129}$ gas. This spin-polarized xenon$^{129}$ gas serves as a contrast medium, allowing the air-to-tissue interfaces of the patient's lungs and bronchial tissues to be imaged very well by the MRI device 12. The mask 18 is connected by tube 16 to an inhalation gas supply apparatus, generally indicated with the numeral 20. The apparatus 20 includes conventional devices (not shown) for providing a life-sustaining mixture of gases, such as a mixture of nitrogen, oxygen, and water vapor, simulating ordinary air.

However, the apparatus 20 also includes apparatus according to the present invention, and which is further described below, for also providing a small amount of spin-polarized xenon$^{129}$ gas as a part of this gas provided to the patient 10 for inhalation. As mentioned above, the requirement for xenon gas for use as such a contrast medium is in the range from only about 1 gram to about 5 grams for each such MRI procedure. Connecting into the apparatus 20 is a pressure container 22 (i.e., a pressurized gas cylinder) or a pair of such cylinders, providing a purified xenon/nitrogen gas mixture. In this mixture, the xenon$^{129}$ isotope constitutes about 26% of the total xenon gas volume, which is the percentage of this isotope in naturally-occurring xenon.

Figure 2A:
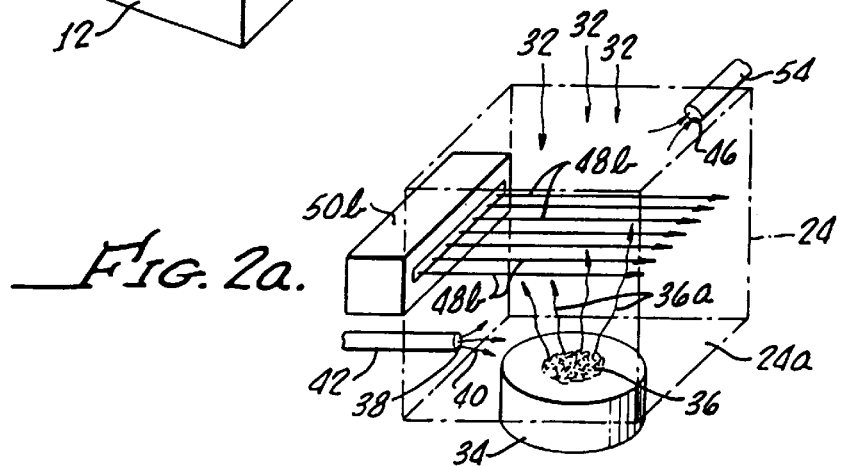
Figure 2:
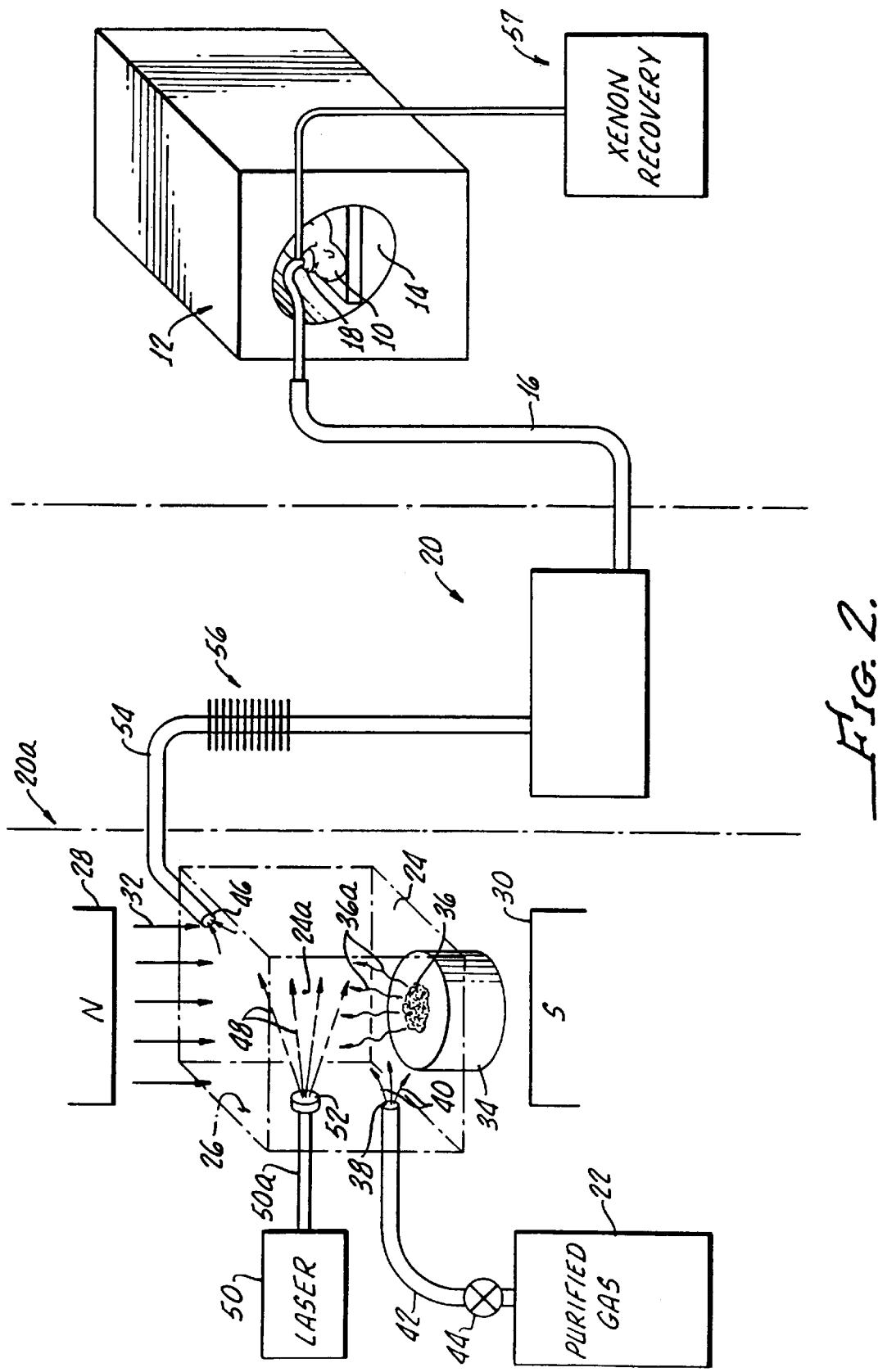

Viewing now FIG. 2, a portion of the apparatus 20 is schematically depicted in greater detail. This portion of the apparatus 20 is indicated with the reference numeral 20a, and is the portion of the apparatus 20 which is used to provide spin-polarized xenon$^{129}$ gas. Apparatus portion 20a includes a non-magnetic and magnetically-permeable reactor vessel 24, which may also be termed a containment vessel because it contains a gas mixture in isolation from ambient and during laser optical pumping as will be described further below. This reactor vessel 24 defines a cavity, indicated with the numeral 24a. The inner surface 26 of vessel 24 (i.e., the surface bounding cavity 24a) is coated with a siliconizing agent in order to make the surface inactive with respect to collision de-excitation of spin polarized gas in the cavity. This vessel 24 is placed between magnetic poles 28, 30 providing a magnetic flux through the cavity 24a (indicated with arrows 32) of about 50 Gauss. Adjacent to a lower extent of cavity 24a is disposed a heater element 34. This heater element is in heat transfer relationship with a quantity 36 (i.e., a quantity of about fractional mg size) of an elemental alkali metal. In this case, preferably, elemental rubidium (Rb) is employed as the alkali metal within the cavity 24a. The heater element 34 maintains the rubidium 36 at a temperature of about 80 to 90 degrees Centigrade. As a result, the rubidium metal 36 vaporizes, and molecules of Rb gas, indicated with arrows 36a, are evolved into cavity 24a.

Also adjacent to the lower extent of cavity 24a, is an inlet port 38 from which issues into the cavity 24a a controlled flow of xenon gas, indicated by arrows 40. The controlled flow of xenon gas mixed with nitrogen gas and indicated by arrows 40 is provided from gas tank 22 (or combination of such tanks, as will be seen) by way of a conduit 42 containing a control valve assembly 44. The vessel 24 provides an outlet port 46 adjacent to the upper extent of the cavity 24a. As a result of this combination of Rb gas from the source 36 and xenon gas from the inlet port 38 adjacent the lower extent of the cavity 24a and of outlet port 38 adjacent to the upper extent of this cavity 24a, an up-welling of these gases together occurs in the cavity 24a. This up-welling of Rb and xenon gases (along with nitrogen gas) occurs in the cavity 24a in the presence of the magnetic field 34.

As the Rb and xenon gases 36a and 40 up-well in the cavity 24a, these gases are bombarded with laser light energy, indicated by arrows 48. The laser light energy is provided by a laser 50, and is admitted to cavity 24a via an optical coupler 50a and divergent lens 52. Preferably, the laser light energy 48 is provided at 794 nm, and with an energy density sufficient to effectively optically pump a significant fraction of the Rb gas 36a. In other words, the laser light energy is tuned to the D1 transition of the Rb gas. In combination with the magnetic field 34 the optical pumping of the Rb gas spin-polarizes a significant fraction of this Rb gas. Preferably, an energy level of 20 watts in band is provided by laser 50. The laser light energy 48 in this embodiment is provided by divergent lens 52 generally in the form of a cone of laser light 50 through which the up-welling of gases flows in cavity 24a.

More preferably, an alternative embodiment of the reactor vessel 24 is depicted. In order to obtain reference numerals for use in describing this alternative embodiment of the reactor vessel, features which are the same in structure or function to those features already introduced are referenced with the same numeral used above. Where necessary to distinguish a feature, a alphabetic suffix may be added to a familiar reference numeral to indicate a feature which is the same or similar in function but is implemented using a different apparatus. As is depicted in FIG. 2a, and for economy of construction and operation of the apparatus 20, the laser light energy 48b is provided by a diode laser bar 50b of sufficient power level and power density that the laser light 48b issues directly into the cavity 24a from this laser light bar without need for the optical coupler 50a and divergent lens 52 as was presented in FIG. 2. This alternative construction of the reactor 24 and cavity 24a is illustrated on FIG. 2a in which the laser light bar 50b is indicated as being present directly adjacent to cavity 24a.

Preferably, this laser light bar 50b may itself form a part of the wall bounding the cavity 24a. In this case, dispersion of the laser light into the cavity 24a is not necessary as was provided by divergent lens 50. Instead, the laser light 48b is distributed inherently by the dispersed production of this light energy by the laser light bar 50b. In this case, the laser light energy 48b extends across cavity 24a transversely to the up-welling of Rb and xenon gas in this cavity, and generally in the form of a sheet or plane of energy through which the up-welling gas must flow. In other words, while the cone-like distribution of laser light in the first embodiment depicted in FIG. 2 possibly would allow some of the up-welling gas to avoid optical pumping, and to avoid being polarized; in the embodiment of FIG. 2a virtually the entire gas flow up-welling in cavity 24a is illuminated and optically pumped by light 48b. Also, coupling of the laser light energy 48b into the cavity 24a is improved with the user of laser light bar 50b because of the immediate access from the laser light bar 50b to the cavity 24a.

In each of the reactor vessel cavities 24a depicted in FIGS. 2 and 2a, as the Rb gas in the cavity 24a is spin-polarized by the laser optical pumping provided by laser light 48 (or 48b) in the presence of magnetic field flux 32, the spin-polarized Rb gas transfers some of its spin energy to the xenon gas by collision between the molecules of these gases. Consequently, the polarized Rb gas spin-polarizes a significant fraction of the xenon gas. As mentioned, a fraction of the xenon gas is xenon$^{129}$ isotope, which when spin polarized is a significant contrast medium for MRI procedures. The Rb and xenon gases together (i.e., some fraction of the gases being spin-polarized and some fraction being not polarized) flow together from the cavity 24a via the outlet port 46.

A conduit 54 connects with outlet port 46 (returning to consideration of FIG. 2) and conveys the mixed Rb and xenon gases to a cryogenic rubidium condenser/separator apparatus, indicated with arrowed reference numeral 56. This cryogenic rubidium condenser/separator apparatus will be described in greater detail below. However, for the present it is sufficient to state that the mixed Rb and xenon gases flowing via conduit 54 from reactor 24 are chilled to a temperature at least as low as −60 degrees Centigrade. As a result, a sufficient fraction of the Rb gas present in the mixed Rb and xenon gases is condensed to a solid form, and is removed from the xenon gas flow, while the xenon gas continues flowing in gaseous form (i.e., the chilling temperature is not sufficiently low to liquify the xenon gas).

This gaseous xenon (still containing the fraction of spin-polarized xenon$^{129}$) is also reheated by the apparatus 56, and passes to patent 10 via the remainder (and conventional) portion of inhalation gas supply device 20. As is seen in FIG. 2, a xenon gas recovery apparatus (generally indicated with the numeral 57) may be provided in association with the mask 18 to receive exhaled gases from the patient 10. In this case, the xenon gas would not be released by exhalation into the ambient environment of the MRI device 12. Thus, possible interference with the imaging provided by the MRI device 12 because of the ambient presence of this exhaled xenon gas (which would still contain a significant fraction of spin-polarized xenon$^{129}$ isotope) is avoided.

Turning now to FIG. 3, a more detailed schematic representation of the reactor vessel 24 (with its associated plumbing) and of the Rb condenser/separator apparatus 56 is presented. As can be seen from the schematic representation of FIG. 3, the gas supply 22 in this case includes a nitrogen gas supply 22a and a xenon gas supply 22b. These gas supplies, 22a and 22b may be provided by separate pressurized gas cylinders, and associated pressure control valves 44a and 44b. These gas supplies 22a and 22b are connected to a conduit 58 along with a gas supply of Helium gas, provided by source 60a (which may also be a pressurized gas cylinder) and pressure control valve 60b. These gas supplies are communicated via a purifier 62, which may include a medical grade filter. This gas supply (i.e., for xenon, nitrogen, and helium gas) is connected by conduit 42 into a gas flow loop, generally indicated by the numeral 64. As is indicated by the arrowed numerals on FIG. 3, part of the loop 64 provides the conduit 42 for gas flow into the reactor 24, while another part of this loop 64 provides the conduit 54 for gas flow from the reactor 24. This gas flow loop 64 includes various control valves 66, 68, 70, 72, 74, and 76 allowing the gas flow loop to be divided into communicated portions while also cutting off communication of other parts of the loop.

Those ordinarily skilled in the pertinent arts will recognize that this arrangement of the apparatus depicted in FIG. 3 allows for cleaning and recharging of the apparatus, for example, with fresh supplies of alkali metal for successive productions of polarized xenon gas. Short circuit conduits 78 and 80 communicate across the loop 64 at selected locations, and are provided respectively with valves 82 and 84 allowing these short circuit conduits to be opened and closed. These short circuit conduits and valves in combination with particular ones of the valves 66–74 allow individual devices in the apparatus to be isolated, or connected only to selected ones of the other devices. In order to allow the cavity 24a to be evacuated, the loop 64 is connected to a vacuum pump 86 via a cryogenic trap 88 (i.e., preventing alkali metal from entering and clogging the vacuum pump) and a conduit 90 including a valve 92.

In order to allow the alkali metallic rubidium to be added to cavity 24, the loop 64 is connected to an alkali ampule loading system 94 via a conduit 96 having a valve 98. The loading system 94 includes an impactor 94a allowing a frangible ampule 100 to be loaded into the loading system 94, and to be fractured after the loading system is closed and communicated to loop 64 via open valve 98. Loop 64 includes a gas analysis device 101. Also in loop 64 as part of the apparatus 56 is disposed a cryogenic cold trap 102 allowing the Rb and xenon gas flows exiting the reactor 24 to be chilled to a temperature of at least −60 degrees Centigrade. More preferably, the temperature to which the mixed Rb and xenon gas flow is chilled is below −60 degrees Centigrade. From the cold trap 102 xenon gas flows by way of valve 72 to a heater 104 in which the xenon gas is warmed to a temperature appropriate for supply to conventional portion of the inhalation gas supply apparatus 20, seen in FIG. 2. This xenon gas flows by way of valve 74 to the exit of loop 64 and to the conventional portion of the gas supply apparatus 20.

Figure 4:
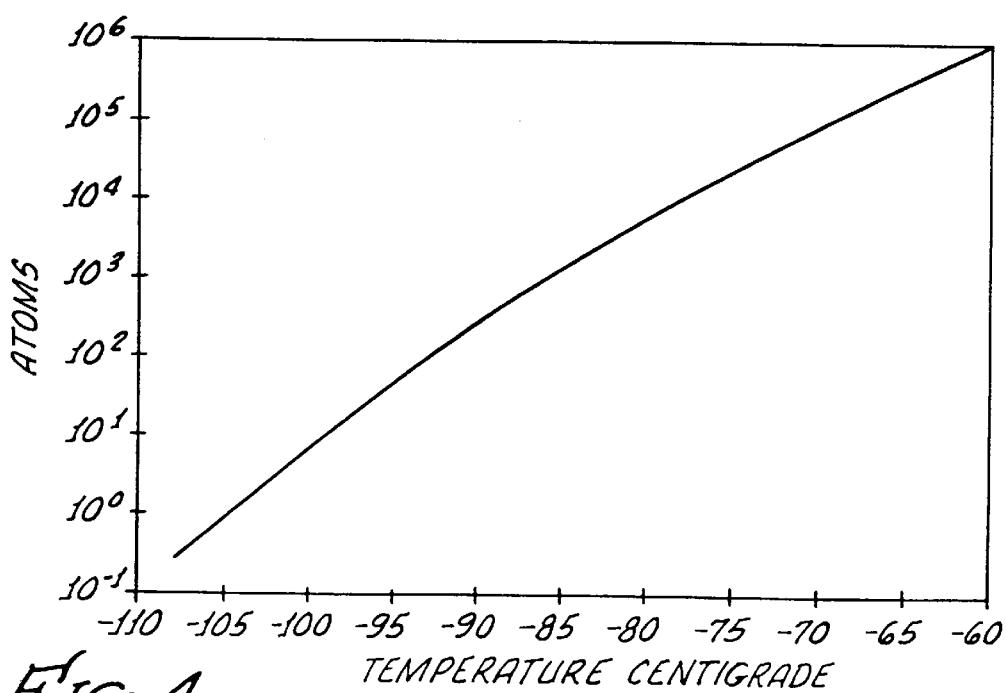

FIG. 4 provides a graphical depiction of the extent of removal of Rb gas molecules from the mixed Rb and xenon gas flow coming from reactor 24. It will be recalled that at STP conditions, the Rb gas (a monatomic molecule) from reactor 24 will have a nominal number of molecules per liter (i.e., about 400 cm$^3$ at STP conditions—which is about one gram atomic weight of Rb in gaseous form) in the $10^{23}$ range (recalling Avogadro's number of $6.02 \times 10^{23}$ atoms per gram atomic weight, or molecules per mole). Viewing FIG. 4, it is seen that at a temperature of −60 degrees Centigrade, the number of Rb molecules will be reduced into about the $10^6$ range (i.e., the Rb is reduced to about one part in $10^{17}$) with the rest of the Rb gas being removed into solid form within the condenser 102. This level of removal of the Rb gas will suffice to make the resulting mixture of Rb and xenon gas of medical-grade purity according to FDA regulations currently in existence or to be promulgated in the future, it is believed.

As FIG. 4 indicates, chilling the xenon and Rb gas flow to even lower temperatures allows even greater removals of the Rb gas from the xenon gas flow passing to patient 10, recalling FIG. 1. In this way, should FDA regulations require a greater removal of the Rb gas than one part in $10^{17}$ in order to meet medical-grade purity requirements, then a lower temperature for cryogenic condensation can be used in condenser 102.

Further to the above, an optical alkali metal diagnostic device 106 is associated with the cold trap 102 in order to allow monitoring of the remaining concentration of alkali metal present in the gas passing to the patient via heater 104. Preferably, this optical diagnostic 106 for residual alkali metal concentration includes a diode laser tuned to the 5S-5P, or 5S-6P transition of Rb gas (indicated with arrowed numeral 108), and a fluorescence detector 110 watching for the light produced by decaying fluorescence (indicated by arrowed numeral 110) of the residue of Rb gas. In this way the residual amount of Rb gas can be diagnosed and maintained below an acceptable level, or treatment of the patient may be terminated if necessary.

While the present invention has been depicted, described, and is defined by reference to a single particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. An apparatus for providing medical-grade spin-polarized xenon$^{129}$ gas, particularly for use as a contrast medium for human inhalation during magnetic resonance imaging procedures, said apparatus comprising:

a reactor vessel defining a cavity for receiving an alkali metal and xenon gas including a fraction of xenon$^{129}$ isotope, said reactor vessel including a heater for gasifying said alkali metal, gas flow means for mixing the xenon gas and alkali metal gases and causing the mixed gases to up-well in said cavity, magnetic means for exposing the mixed alkali metal and xenon gases to a magnetic field, laser means for optically pumping the mixed and up-welling alkali metal and xenon gases with laser light energy to spin-polarize a significant fraction of the alkali metal gas, said spin-polarized alkali metal gas transferring spin energy to the xenon gas by molecular collision between alkali metal gas molecules and xenon gas molecules in the mixed gases to provide a significant fraction of spin-polarized xenon gas including spin-polarized xenon$^{129}$ gas, said gas flow means including means for flowing the mixed gases including said spin-polarized xenon$^{129}$ gas together from said reactor vessel;

cryogenic alkali metal gas condensation and separation means including a gas flow means for receiving the mixed alkali metal and xenon gases, for chilling these mixed gases to a temperature of at least −60 degrees Centigrade or lower and condensing said alkali metal gas to a solid form, and for allowing continued flow to an exit of xenon gas including said spin-polarized xenon$^{129}$ gas.

2. The apparatus of claim 1 wherein said reactor vessel defines an inner surface, and a coating of siliconizing material on said inner surface of said reactor vessel.

3. The apparatus of claim 1 wherein said laser means for optically pumping the mixed alkali metal and xenon gases with laser light energy to spin-polarize a significant fraction of the alkali metal gas includes a diode laser light bar.

4. The apparatus of claim 3 wherein said laser light bar forms a part of said reactor vessel bounding an inner cavity of said vessel within which said mixed gases are contained in isolation from ambient.

5. The apparatus of claim 4 wherein said laser light bar provides a plane of laser light energy traversing said cavity and through which gas flow up-welling in said cavity must flow to be optically pumped.

6. The apparatus of claim 1 wherein said gas flow means includes said reactor vessel defining a gas flow inlet port to said cavity adjacent a lower extent thereof for receiving a flow of xenon gas, and a gas flow outlet port adjacent an upper extent of said cavity for discharging a mixed flow of alkali metal and xenon gases.

7. The apparatus of claim 6 wherein said gas flow means includes said heater being disposed adjacent to a lower extent of said cavity to mix gaseous alkali metal with said flow of xenon gas received via said inlet port.

8. The apparatus of claim 1 wherein said laser means for optically pumping the mixed and up-welling alkali metal and xenon gases with laser light energy to spin-polarize a significant fraction of the alkali metal gas includes a laser light source disposed vertically along a height dimension of said cavity between said inlet and said outlet port, said laser light source directing laser light energy across said cavity generally horizontally to illuminate and optically pump mixed alkali metal and xenon gases up-welling within said cavity.

9. The apparatus of claim 1 further including conduit structure forming a conduit loop, said conduit loop communicating with said reactor vessel cavity and said cryogenic alkali metal gas condensation and separation means, said conduit loop further including means for introducing a source of alkali metal into said reactor vessel cavity.

10. The apparatus of claim 9 wherein said means for introducing a source of alkali metal into said reactor vessel cavity includes an alkali metal loading chamber for receiving and selectively breaking a frangible ampule containing alkali metal.

11. The apparatus of claim 9 wherein said means for introducing a source of alkali metal into said reactor vessel cavity further includes said conduit loop including connection with a vacuum pump, and connection with a source of inert transport gas, whereby said transport gas is admitted to said alkali metal loading chamber, said chamber is purged with transport gas, and vacuum is used after said ampule is broken to impel movement of said alkali metal and transport gas into said reactor vessel cavity.

12. A method of providing spin-polarized xenon$^{129}$ gas, said method comprising steps of:

providing a reactor vessel defining a cavity introducing a quantity of an alkali metal into a lower portion of said cavity;

heating said alkali metal to produce alkali metal gas;

introducing xenon gas including a fraction of xenon$^{129}$ isotope into a lower portion of said cavity;

causing mixing and up-welling of the alkali metal gas and xenon gas within said cavity;

providing a magnetic field traversing said cavity and said mixed and up-welling alkali metal and xenon gases;

illuminating and optically pumping said mixed and up-welling alkali metal and xenon gases with laser light energy traversing said cavity generally perpendicularly to said up-welling gas flow to spin-polarize a significant fraction of the alkali metal gas;

colliding molecules of said alkali metal gas with molecules of said xenon gas to transfer spin energy from said spin-polarized alkali metal gas to said xenon gas to provide a significant fraction of spin-polarized xenon$^{129}$ gas;

flowing the mixed alkali metal and xenon gases including said spin-polarized xenon$^{129}$ gas together from said reactor vessel; and cryogenically condensing said alkali metal gas and separating the xenon gas from the condensed alkali metal to provide a flow of xenon gas including said spin-polarized xenon$^{129}$ gas.

13. The method of claim 12 further including the step of providing a coating of siliconizing material on an inner surface of said cavity.

14. The method of claim 12 further including the step of using a laser light bar to optically pump said mixed and up-welling alkali metal and xenon gases in said cavity.

15. The method of claim 14 further including the step of using said laser light bar to provide a plane of laser light energy traversing said cavity generally perpendicularly to flow of said mixed and up-welling alkali metal and xenon gases in said cavity.

16. The method of claim 14 further including the step of using said laser light bar to form a part of a boundary for said reactor vessel bounding said cavity.

17. The method of claim 12 further including the steps of configuring said reactor vessel cavity to define a gas flow inlet port adjacent a lower extent thereof, receiving the flow of xenon gas at said gas flow inlet port, defining a gas flow outlet port adjacent an upper extent of said cavity, and discharging said mixed flow of alkali metal and xenon gases at said gas flow outlet port.

18. An apparatus for providing medical-grade spin-polarized xenon$^{129}$ gas, particularly for use as a contrast medium for human inhalation during magnetic resonance imaging procedures, said apparatus comprising:

a reactor vessel, said reactor vessel defining a cavity for receiving an alkali metal and xenon gas including a fraction of xenon$^{129}$ isotope, said reactor vessel including a heater disposed at a floor of said reactor vessel for gasifying said alkali metal, gas inflow and outflow means for receiving and discharging the xenon gas into and from said cavity, said gas inflow and outflow means providing for mixing of said alkali metal gas with said xenon gas to up-well the mixed gases in said cavity;

magnetic means providing a magnetic field traversing said cavity and said mixed flow of alkali metal and xenon gases up-welling in said cavity;

laser means for projecting laser light energy across said cavity generally horizontally to illuminate said up-welling mixed alkali metal and xenon gases to optically pumping these gases spin-polarize a significant fraction of the alkali metal gas, said spin-polarized alkali metal gas transferring spin energy to the xenon gas by molecular collision between alkali metal gas molecules and xenon gas molecules in the mixed and up-welling gases to provide a significant fraction of spin-polarized xenon gas including spin-polarized xenon$^{129}$ gas;

cryogenic alkali metal gas condensation and separation means including a gas flow means for receiving the mixed alkali metal and xenon gases, for chilling these mixed gases to a temperature of at least −60 degrees Centigrade or lower and condensing said alkali metal gas to a solid form, and for allowing continued flow to an exit of xenon gas including said spin-polarized xenon$^{129}$ gas;

said laser means including a diode laser light bar providing a plane of laser light energy traversing said cavity and through which substantially all of said mixed alkali metal and xenon gas flow up-welling in said cavity must flow to be optically pumped.

19. The apparatus of claim 18 wherein said laser light bar forms a part of the boundary surface for said reactor vessel cavity.

20. The apparatus of claim 18 further including a diagnostic device for detecting the level of residual alkali Rb metal gas present in said spin-polarized xenon$^{129}$ gas flowing to said exit, said diagnostic device including:

a diode laser illuminating said spin-polarized xenon$^{129}$ gas flowing to said exit and tuned to a transition of Rb gas selected from the group consisting of: the 5S-5P transition, and 5S-6P transition; and a fluorescence detector directed to detect light produced by decaying fluorescence of said residue of Rb gas in said spin-polarized xenon$^{129}$ gas flowing to said exit.

* * * * *